United States Patent [19]

Le Compagnon

[11] Patent Number: 5,097,696
[45] Date of Patent: Mar. 24, 1992

[54] METHOD AND APPARATUS FOR DETERMINING SLIDING RESISTANCE

[75] Inventor: Gilles Le Compagnon, Dover, N.H.

[73] Assignee: Harvard Industries-The Kingston Warren Corp., Newfields, N.H.

[21] Appl. No.: 547,781

[22] Filed: Jul. 3, 1990

[51] Int. Cl.⁵ ............................................. G01N 19/02
[52] U.S. Cl. .......................................................... 73/9
[58] Field of Search ......................................... 73/9, 10

[56] References Cited

U.S. PATENT DOCUMENTS

| | | | |
|---|---|---|---|
| 3,535,911 | 10/1970 | Armstrong et al. | 73/9 |
| 4,424,710 | 1/1984 | Von Nortwick, II | 73/9 X |
| 4,622,712 | 11/1986 | Sugita et al. | 15/250.36 |
| 4,677,188 | 6/1987 | Utsumi et al. | 264/176.1 X |
| 4,912,803 | 4/1990 | Yasukawa et al. | 15/250.36 |

Primary Examiner—Tom Noland
Attorney, Agent, or Firm—Lahive & Cockfield

[57] ABSTRACT

A method and apparatus are disclosed for determining sliding resistance between a surface of a portion of a glass section and a surface of a strip of resilient material, such as an elastomeric weatherstrip, which defines a channel having a longitudinal axis. The apparatus includes a plate which is slidably engaged with a platform and structure for rigidly securing at least one strip of weatherstrip to the plate. Further included in the disclosed apparatus is a device for exerting on the glass section a plurality of forces relative to gravity so that the portion of the glass section passes at a selected rate through the channel along the channels longitudinal axis. Friction between the surface of the glass section and surface of the strip of resilient material results in a portion of the exerted force being transmitted to the plate. A force measuring device, which is coupled to the platform, measures the portion of the force exerted on the glass section that is transmitted to the plate. The disclosed method of the invention includes the steps of securing at least one strip of resilient material to a plate so that force exerted on the strip is transmitted to the plate and exerting on a glass section a force so that a portion of the glass section passes at a selected rate through a channel defined by the strip of resilient material. A portion of the force exerted on the glass section which is transmitted to the plate by friction between the surface of the glass section and the surface of the strip of resilient material is measured and represents sliding resistance.

15 Claims, 2 Drawing Sheets

METHOD AND APPARATUS FOR DETERMINING SLIDING RESISTANCE

BACKGROUND OF THE INVENTION

The present invention relates generally to testing the characteristics of elastomeric weatherstrips. In particular the invention is concerned with a method and apparatus for determining the sliding resistance between an extruded elastomeric weatherstrip and a glass section being passed through a channel defined by the weatherstrip.

Extruded elastomeric weatherstrips are commonly used to provide sealing between the edges of openings of motor vehicle bodies and closure elements for those openings. These weatherstrips are particularly well suited for providing protection from air, water, and dust passing through window seams. To perform effectively, the weatherstrips must be manufactured to given specifications.

An elastomeric weatherstrip designed for use between a window and a door pillar section of a motor vehicle body typically includes a channel for guiding the window and a sealing section for providing sealing between the two components. An important characteristic of such an elastomeric weatherstrip, is the amount of resistance that it provides a window being urged through the channel while the window is being either opened or closed. This is referred to as sliding resistance and is equivalent to the friction force generated between the surface of the weatherstrip that defines the channel and the surface of the glass section being urged through the channel.

If the channel is too narrow, sliding resistance will be high and the force required to drive the window through the channel will be excessive. This results in the task of manually opening or closing the window being unduly burdensome to the operator. In he case of motor-driven windows, too high sliding resistance between the window and the channel will prevent the motor from closing the window.

If the channel is too wide, the sliding resistance between the window and the channel will be low but the sealing provided therebetween will be poor. It is important therefore, that the channel defined by a weatherstrip as used on the pillar section of an automobile door frame be properly formed so that effective sealing is provided between the window and the door pillar section but excessive force is not required to drive the window through the channel.

It is, therefore, an object of the present invention to provide a method and apparatus for simply and economically measuring sliding resistance. It is another object of the present invention to enable a manufacturer of elastomeric weatherstrips to monitor the sliding resistance of manufactured weatherstrips.

SUMMARY OF THE INVENTION

The problems associated with known methods and apparatuses for testing characteristics of elastomeric weatherstrips are greatly relieved by the present invention which allows accurate gathering of data relating to an important characteristic of elastomeric weatherstrips, i.e. sliding resistance. By providing this data simply and economically, the present invention encourages the manufacture of high quality weatherstrips having improved sealing capabilities.

In one aspect, the invention includes an apparatus for measuring the sliding resistance between a surface of a portion of a glass section and the surface of a strip of resilient material such as an elastomeric weatherstrip. The sliding resistance is engendered when the glass is driven through a channel defined by the surface of the weatherstrip. In this aspect, the invention includes a plate which is slideably engaged with a platform and a device for securing at least one strip of the weatherstrip to the plate so that force exerted on the strip is transmitted to the plate. The apparatus further includes components for exerting on the glass section a plurality of forces relative to gravity so that a portion of the glass section passes at a selected rate through the channel defined by the weatherstrip along the channel's longitudinal axis. As a result, friction between the surface of the glass section and the surface of the strip of weatherstrip results in a portion of the force which is exerted on the glass section, being transmitted to the plate. The apparatus includes a force measuring device, such as a load cell, which is coupled to the platform for measuring the portion of the force exerted on the glass section which is transmitted to the plate.

In one embodiment the invention includes structure for rigidly securing at least two strips of weatherstrip to the plate so that separate portions of a glass section can be passed through channels defined by the two weatherstrips simultaneously. In this embodiment, the invention is able to accurately determine the sliding resistance as it most closely resembles that which will be experienced during actual use of the weatherstrips.

An illustrative embodiment of the invention includes a motor which rotates a spool and a line which is wound around the spool and connected to the glass section. These components are utilized for exerting a force on the glass section to move it counter to gravity through the channel(s) defined by the weatherstrip(s). By rotating the spool in a first direction, the motor causes the line to be wound around the spool which results in a force being applied to the glass section which is counter to and greater than gravity. Rotation of the spool in a second direction results in the line being unwound from the spool. This causes a force to be exerted on the glass section which is counter to and less than gravity.

In order to most accurately determine sliding resistance as it will be experienced during actual use of the tested weatherstrips, the apparatus includes structure for enabling the weatherstrips to be oriented both vertically as well as to be oriented angularly offset from vertical. Also included is a device, such as a protractor, for determining the extent to which the weatherstrips are angularly offset from vertical.

In another aspect, the invention is a method for determining the sliding resistance between a surface of a portion of a glass section and a surface of a strip of resilient material such as an elastomeric weatherstrip. In this aspect, the invention includes the steps of securing the strip of elastomeric material to a plate so that force exerted on the strip is transmitted to the plate. This aspect of the invention also includes the step of exerting on the glass section, a force relative to gravity so that a portion of the glass section passes at a selected rate through a channel defined by the weatherstrip. Friction between the surface of the glass section and the surface of the weatherstrip results in a portion of the force exerted on the glass section being transmitted to the plate. By measuring the force transmitted to the plate, the method of the present invention determines sliding resistance.

In one embodiment, the method of the invention includes the step of securing a second strip of resilient material to the plate so that separate portions of the glass section pass through the channels defined by the strips of resilient materials simultaneously. In this embodiment, by duplicating the application in which the weatherstrips being tested are actually used, the invention is able to accurately determine sliding resistance as it will be experienced in the field.

These and other advantages of the present invention are more fully explained in the following detailed description which references the attached drawing.

DETAILED DESCRIPTION

In one aspect the invention is an apparatus for determining the force exerted on a strip of resilient material, such as a weatherstrip, when a portion of a glass section is passed at a selected rate along a longitudinal axis of a channel defined by the strip. The invention includes structure for supporting at least one strip of the weatherstrip, a work unit for urging a glass section through the channel defined by the strip of the weatherstrip, and a device for determining the force exerted on the weatherstrip.

Figure 1:
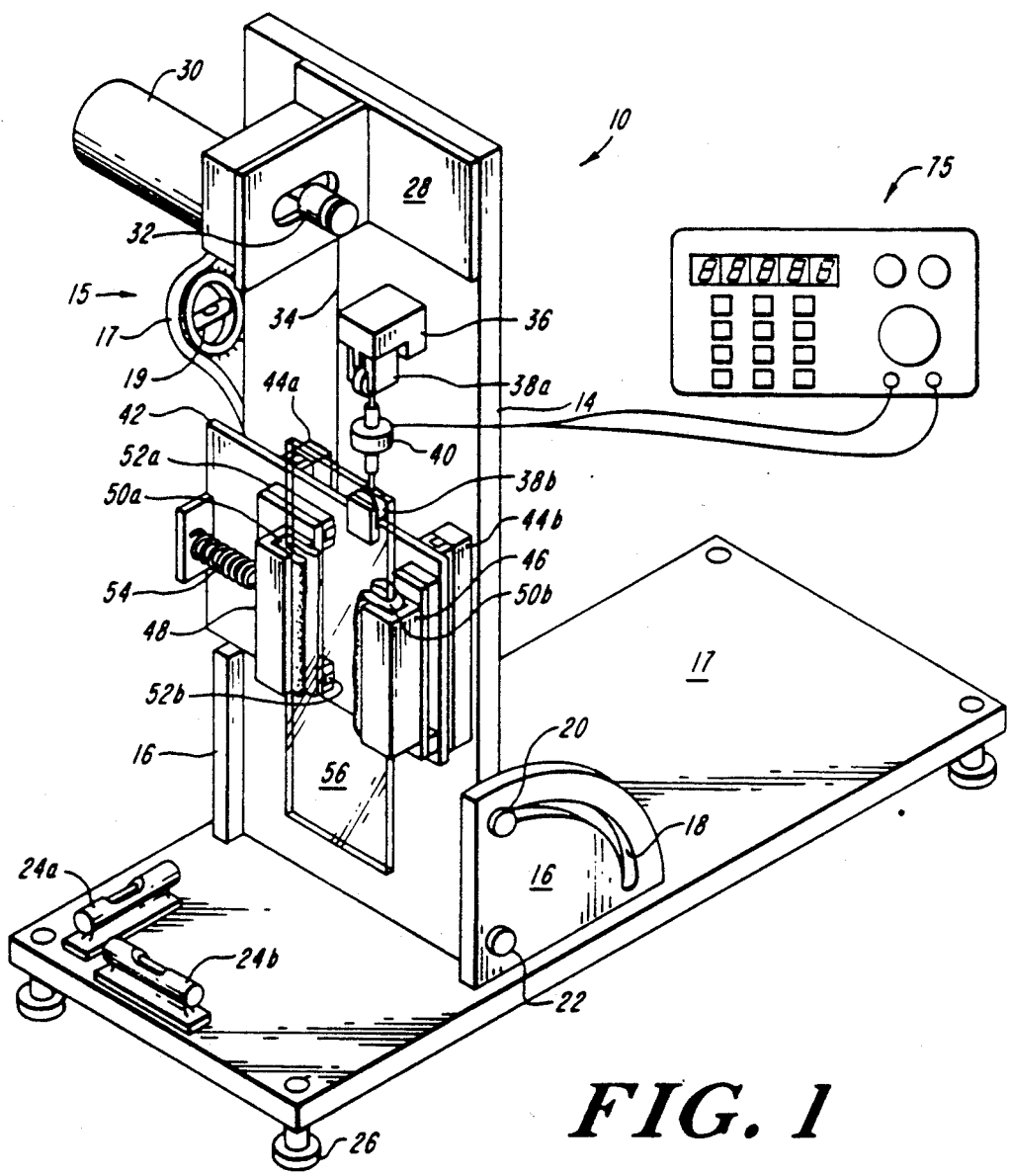
FIG. 1 is a perspective view of an apparatus constructed in accordance of the teaching of the present invention.

FIG. 1 shows an illustrative embodiment of an apparatus 10 constructed in accordance with the present invention. Apparatus 10 includes a horizontal base plate 12 which supports an upright platen 14. Respectively, each of two platen brackets 16 defines an arcuate slot 18 within which travels a thumb screw 20 which is connected to platen 14. Platen brackets 16 define a rotation axis 22 around which the upright platen 14 is rotatable. Thumb screws 20 are adjustable to control the orientation of the upright platen 14 along the arcuate slot 18. In this manner, the upright platen 14 can be manipulated to simulate the orientation in which the weatherstrip to be tested will be used.

Mounted on base plate 12 are two leveling devices 24a and 24b for ensuring that during testing of a weatherstrip the base plate 12 is properly oriented. To account for the apparatus 10 being placed on an irregular surface, base plate 12 is supported by adjustable feet 26, the heights of which can be independently varied.

Mounted on platen 14 is a protractor 15 which includes a frame 17 and a level indicator 19. After thumb screws 20 have been adjusted in arcuate slots 18 to properly orient platen 14, the degree to which platen 14 is offset from vertical can be determined by rotating level indicator 19 within frame 17 so that level indicator 19 is horizontal. The orientation of frame 17, and hence of platen 14, can then be read from markings on frame 17.

A motor mount 28 is secured to the top of upright platen 14 and supports a motor 30. Motor 30 is arranged to drive a spool 32 around which is wound a line 34. Also secured to the upright platen 14 is a load cell bracket 36 which, via a coupling 38a, supports a force measuring device such as a load cell 40. Load cell 40 is connected via a coupling 38b to a frictionless slide plate 42 which is capable of frictionless reciprocation with respect to platen 14. Ball slide guides 44a and 44b are rigidly affixed to upright platen 14 and restrict the movement of frictionless slide plate 42 to a vertical axis. To prevent insulating load cell 40 from forces exerted on frictionless slide plate 42, ball slide guides 44a and 44b have an extremely small coefficient of friction. This coefficient of friction will typically be approximately 0.003. As a result, of any force applied to frictionless slide plate 42, the component parallel to platen 14 will be truly transmitted to load cell 40 via coupling 38b.

A stationary weatherstrip holder 46 is rigidly secured to frictionless slide plate 42. Also secured to frictionless slide plate 42 is a movable weatherstrip holder 48 which, as guided by weatherstrip holder guides 52a and 52b, is capable of linear movement along a transverse axis with respect to frictionless slide plate 42. In one embodiment, spring 54 acts on movable weatherstrip holder 48 to urge it toward stationary weatherstrip holder 46. A glass section 56 is placed between the weatherstrip holders 46 and 48 for traveling between opposed channels defined by weatherstrips 50a and 50b which are held by weatherstrip holders 46 and 48. Spring 54 is selected based on its magnitude so that glass section 54 experiences a compressive force exerted by movable weatherstrip holder 48 which closely simulates that force which is exerted by the pillar section of an automobile door. Typically, this will result in a spring having a spring coefficient varying between 0.1 and 0.6 N/mm.

In another embodiment, movable weatherstrip holder 48 can be stationarily secured with respect to frictionless slide plate 42 simply by screws (not shown). This can be done after glass section 56 has been properly positioned. Again, the position of spring loaded weatherstrip holder 48 will be selected in order to simulate the compressive force exerted on glass section 56 that is typical of the actual use of the weatherstrip 50.

For determining sliding resistance of a given weatherstrip profile, apparatus 10 is utilized in the following manner. A strip of weatherstrip is secured to each of the weatherstrip holders 46 and 48 so that channels defined by the weatherstrips face inwardly. It will be appreciated that the weatherstrip holders 46 and 48 can be constructed in various configurations for securing a variety of weatherstrips having a variety of profiles. Also, while the sliding resistance test will typically be performed in conjunction with two weatherstrips, it is anticipated that with a proper guide to insure the equilibrium of glass section 56 during testing, the test can also be performed with only one strip of weatherstrip. In both cases, the results can be analogized by breaking down total sliding resistance into a "per unit length of weatherstrip" value. That is, for example, total sliding resistance for one 100 mm strip of weatherstrip will be half that for two 100 mm strips of weatherstrip. By breaking down data obtained in conjunction with both of these tests to sliding resistance per 100 mm of weatherstrip, the final results of both tests are the same.

If the positioning of movable weatherstrip 48 is to be controlled by a spring, at this point the spring will be installed. After spring 54 has been installed, glass section 56 is guided into the channels defined by the weatherstrips 50a and 50b. If a spring is not used, after glass section 56 has been guided into the channels defined by weatherstrips 50a and 50b, movable weatherstrip holder 48 is screwed in place. The line 34, which is permanently attached to glass section 56, is wound around spool 32 and the apparatus 10 is thereby prepared for use.

Once the apparatus has been so prepared, motor 30 is activated to unwind line 34 from spool 32 so that gravity causes glass section 56 to lower to its start position. If the weight of glass section 56 is such that it will not fall freely, the operator can gently pull downward on glass section 56 while motor 30 is rotating spool 32. Once glass section 56 has reached its start position, motor 30 is reversed so that spool 32 rotates to cause line 34 to be wound around it. This results in the free length of line 34 being shortened thereby exerting a force on glass section 56 which is greater than and counter to the force exerted on glass section 56 by gravity. As a result, glass section 56 travels up toward motor 30 while passing through the channels defined by weatherstrip sections 50a and 50b.

During this movement, friction between the outer surface of glass section 56 and the surfaces of weatherstrips 50a and 50b defining the channels will result in an upward force being exerted on weatherstrips 50a and 50b and, hence, on weatherstrip holders 46 and 48. This force is transmitted to frictionless slide plate 42. Due to the extremely small coefficient of friction between frictionless slide plate 42 and ball slide guides 44a and 44b, the force is further transmitted to load cell 40.

Load cell 40 delivers a signal to display unit 75 which is calibrated to display the force exerted by movement of glass section 56 through the channels defined by weatherstrips 50a and 50b on load cell 40. This calibration includes adjusting the readout of display unit 75 so that the force exerted on load cell 40 by the weight of frictionless slide plate 42 reads as 0. The difference between these forces, which is attributed to the friction between glass section 56 and weatherstrips 50a and 50b, is therefore displayed by display unit 75.

In one embodiment of the invention, display unit 75 communicates with a chart recorder (not shown) which records the force detected by load cell 40 in relation to time. Such an arrangement is particularly useful for monitoring sliding resistance over the full range of movement of glass section 56.

Figure 2:
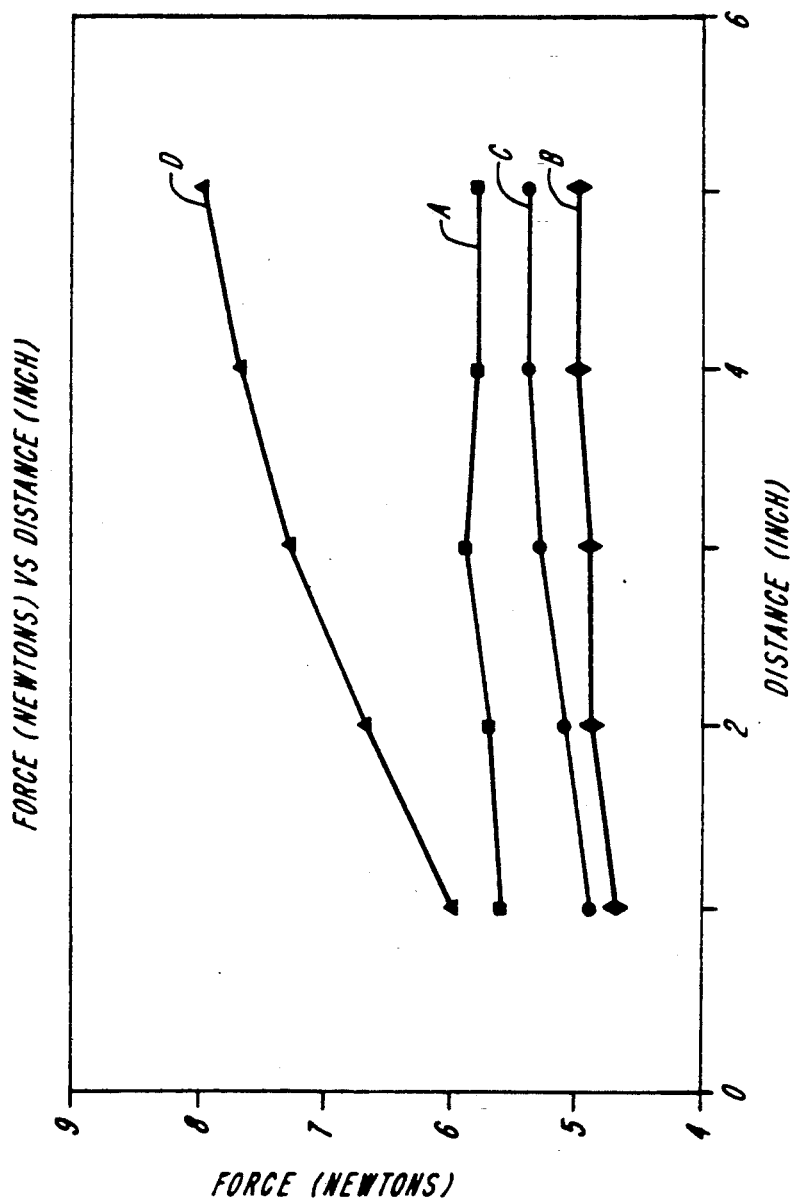
FIG. 2 is a graph of data collected in conjunction with the use of the apparatus depicted in FIG. 1.

Sliding resistance is determined based on tests performed by apparatus 10 involving glass sections of various thicknesses and various character. Typically, this involves testing the same strips of weatherstrip with glass sections of both 4 mm and 5 mm thickness and having dry and wet surfaces. FIG. 2 is a graphic illustration of sliding resistance per 100 mm of weatherstrip channel based on data acquired in conjunction with such a battery of tests.

In the figure, lines A and B represent data acquired while utilizing apparatus 10 in accordance with the above described technique with a 4 mm thick glass section. Lines C and D represent data acquired in connection with a 5 mm thick glass section. Moreover, lines A and C represent sliding resistance for a glass section having a wet outer surface, while lines B and D represent sliding resistance for a glass section having a dry outer surface. The graph shows that thicker glass sections engender higher sliding resistance than do thinner glass sections and that glass sections having dry outer surfaces engender higher sliding resistance than do glass sections having wet outer surfaces.

In order to manufacture weatherstrips that provide effective sealing between windows and the edges of openings in automobile bodies, it is important that sliding resistance be properly maintained. This can be achieved by systematically testing sample weatherstrips during manufacturing runs, and implementing statistical process controls so that aberrations in weatherstrip quality are discovered and can be addressed. By providing a fast and simple way to monitor sliding resistance, therefore, the present invention enables weatherstrips to be manufactured the quality of which is closely controlled. Also, by determining sliding resistance on a per unit length basis, total sliding resistance for a given application can be extrapolated. This allows an engineer in the design stage to select the proper electrical drive motor for that application. The present invention provides a simple, effective, and economic way for performing a sliding resistance test so that a manufacturer utilizing the present invention can produce superior weatherstrips having proper sliding resistance.

It should be understood that the above-described embodiments are merely illustrative of the present invention and that various alterations and additional applications will be readily apparent to those skilled in the art. The invention is to defined, therefore, not by the preceeding description but by the claims that follow.

What is claimed is:

1. An apparatus for determining the sliding resistance between a surface of a portion of a glass section subject to a force exerted by gravity and a surface of a first strip of resilient material, the surface of the strip of resilient material defining a channel having a longitudinal axis, the apparatus comprising a plate slideably engaged with a platform, means for rigidly securing the first strip of resilient material to said plate so that force exerted on the strip is transmitted to the plate;

means for exerting on the glass section a plurality of forces relative to gravity so that the portion of the glass section passes at a selected rate through the channel along the channel's longitudinal axis according to the respective one of the plurality of forces then applied, friction between the surface of the glass section and the surface of the strip of resilient material resulting in a portion of the force then applied being transmitted to the plate; and means coupled to the platform for measuring the portion of the then applied force that is transmitted to the plate.

2. An apparatus as set forth in claim 1 further comprising means for rigidly securing to the plate a second strip of resilient material defining a channel having a longitudinal axis so that the longitudinal axes of the channels defined by said first and second strips are arranged to be parallel to one another, the glass section being arranged so that separate portions of the glass section pass through each channel simultaneously.

3. An apparatus as set forth in either of claim 1 or claim 2 wherein said means for exerting on the glass section a plurality of forces comprises a motor which rotates a spool, and a line which is wound around said spool and which is connected to the glass section, rotation of said spool in a first direction resulting in said line being wound around said spool and thereby exerting a first of said plurality of forces on the glass section, the first force being greater than and counter to the force exerted on the glass section by gravity, and rotation of said spool in a second direction resulting in said line being unwound from said spool, and thereby exerting a second of said plurality of forces on the glass section, said second force being less than the counter to the force exerted on the glass section by gravity.

4. An apparatus as set forth in claim 1 wherein said means for measuring the portion of the then applied force transmitted to said plate is a strain gage coupled at one end to the platform and at an opposite end thereof in communication with said plate.

5. An apparatus as set forth in claim 1 wherein said means for rigidly securing the strip of resilient material is configured to orient the channel relative to vertical.

6. An apparatus as set forth in claim 1 wherein said means for rigidly securing the strip of resilient material is configured to orient the channel angularly offset from vertical.

7. An apparatus as set forth in claim 6 further including,
means for determining the extent to which the channels are angularly offset from vertical.

8. An apparatus as set forth in claim 7 wherein said means for determining the extent to which the channels are angularly offset from vertical is a protractor the orientation of which is related to the orientation of the channel.

9. A method for determining the sliding resistance between a surface of a portion of a glass section subject to a force exerted by gravity and a surface of a first strip of resilient material, the surface of the strip of resilient material defining a channel having a longitudinal axis, the method comprising the steps of:
securing to a plate which is slideably engaged with a platform a first strip of elastomeric material so that force exerted on the strip is transmitted to the plate, said first strip of elastomeric material forming said first strip of resilient material;
exerting on the glass section a plurality of forces relative to gravity so that the portion of the glass section passes at a selected rate through the channel along the channel's longitudinal axis according to the respective one of the plurality of forces then applied, friction between the surface of the glass section and the surface of the strip of resilient material resulting in a portion of the force then applied being transmitted to the plate; and
measuring the portion of the then applied force that is transmitted to the plate.

10. A method as set forth in claim 9 further comprising the step of securing to the plate a second strip of resilient material defining a channel having a longitudinal axis to the plate so that the longitudinal axes of the channels defined by said first and second strips are aligned to be parallel to one another, separate portions of the glass section being passed through each channel simultaneously.

11. A method as set forth in claim 10 further comprising the step of
orienting said first and second strips relative to vertical.

12. A method as set forth in claim 10 further comprising the step of
orienting said first and second strips angularly offset from vertical.

13. A method as set forth in claim 9 wherein the step of exerting on the glass section a plurality of forces is performed by rotating with a motor a spool, a line being wound around the spool and connected to the glass section so that rotation of the spool in a first direction results in the line being wound around the spool and thereby exerting a first of said plurality of forces on the glass section, said first force being greater than and counter to a force exerted by gravity, and rotation of the spool in a second direction resulting in the line being unwound from the spool and thereby exerting on the glass section a second of said plurality of forces, said second force being less than and counter to gravity.

14. A method as set forth in claim 9 further comprising the step of
orienting said first strip relative to vertical.

15. A method as set forth in claim 9 further comprising the step of
orienting said first strip angularly offset from vertical.

* * * * *